United States Patent [19]

Hillstead

[11] Patent Number: 5,037,392
[45] Date of Patent: Aug. 6, 1991

[54] STENT-IMPLANTING BALLOON ASSEMBLY

[75] Inventor: Richard A. Hillstead, Miramar, Fla.

[73] Assignee: Cordis Corporation, Miami, Fla.

[21] Appl. No.: 362,253

[22] Filed: Jun. 6, 1989

[51] Int. Cl.$^5$ ............................................. A61M 25/00
[52] U.S. Cl. ..................................... 604/96; 606/191; 606/194
[58] Field of Search ................. 606/191, 194, 98, 200; 604/96

[56] References Cited

U.S. PATENT DOCUMENTS

| | | | |
|---|---|---|---|
| 4,141,364 | 2/1979 | Schultze | 604/96 |
| 4,406,656 | 9/1983 | Hattler et al. | 604/96 X |
| 4,580,568 | 2/1986 | Gianturco | 606/198 |
| 4,655,771 | 4/1987 | Wallsten | 623/1 |
| 4,800,882 | 1/1989 | Gianturco | 606/194 |

Primary Examiner—Robert A. Hafer
Assistant Examiner—Kerry Owens
Attorney, Agent, or Firm—Henry W. Collins; Thomas R. Vigil

[57] ABSTRACT

The dilatation balloon assmebly comprises a catheter having a proximal end, a distal end and a distal end portion, the distal end portion having openings in the side wall thereof, and a dilatation balloon connected to and extending from the distal end of the catheter around and about the distal end portion of the catheter to a proximal end of the balloon which is also connected to the catheter. The balloon has at least three axially extending longitudinal creases therein whereby, when the balloon is in a deflated state, the maximum lateral extent in cross-section of the balloon is less than the diameter or lateral extent of a fully inflated balloon or a partially inflated balloon.

9 Claims, 2 Drawing Sheets

U.S. Patent     Aug. 6, 1991     Sheet 1 of 2     5,037,392
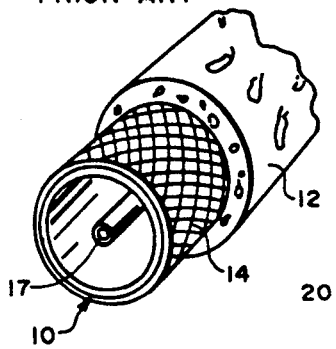
*FIG. 1A* PRIOR ART
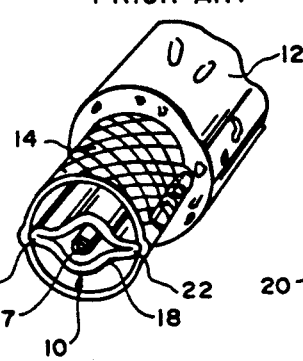
*FIG. 1B* PRIOR ART
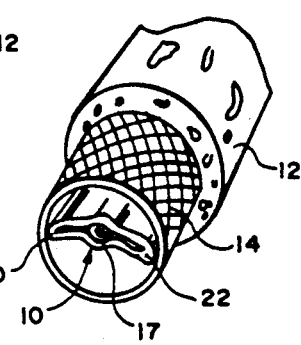
*FIG. 1C* PRIOR ART
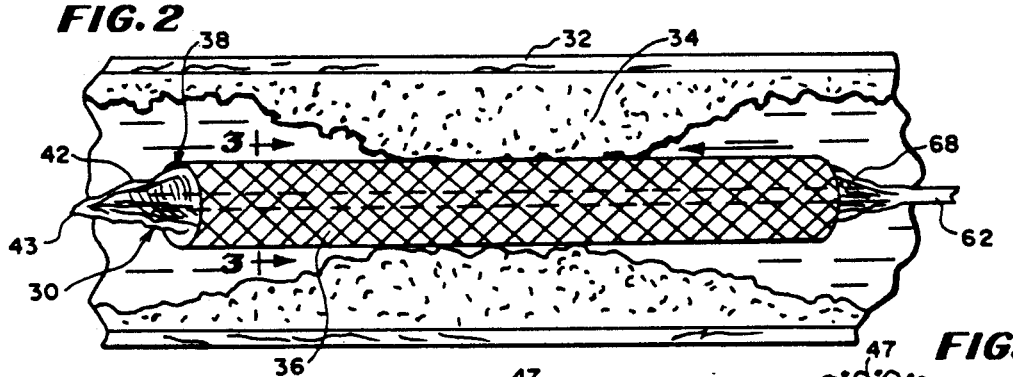
*FIG. 2*
*FIG. 3*
*FIG. 4*
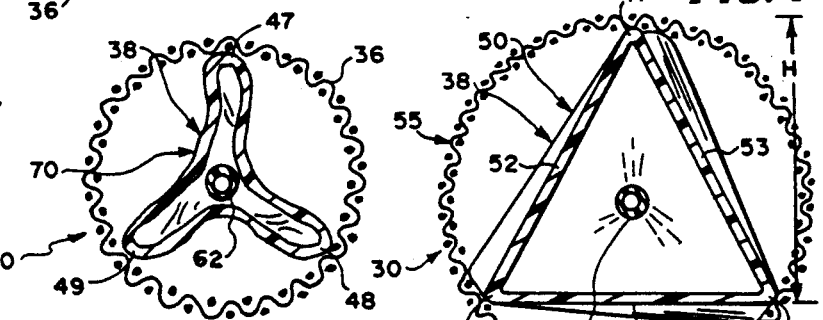
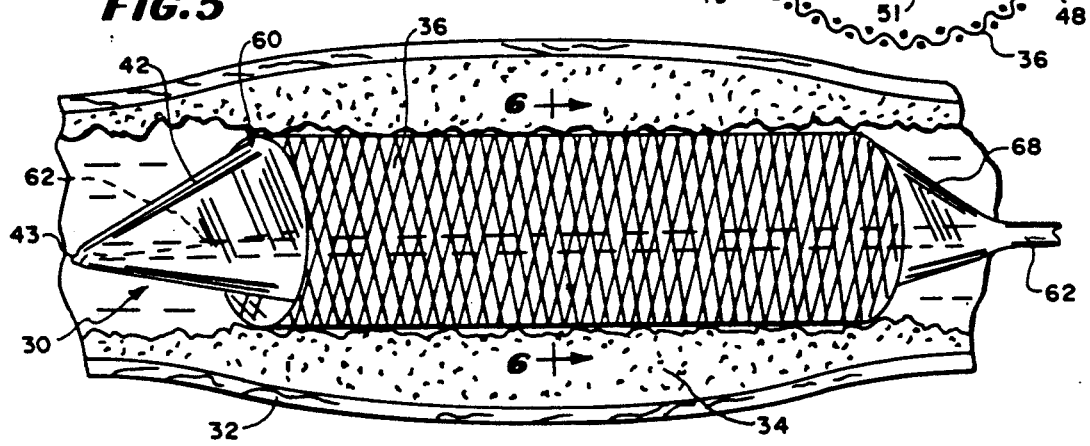
*FIG. 5*

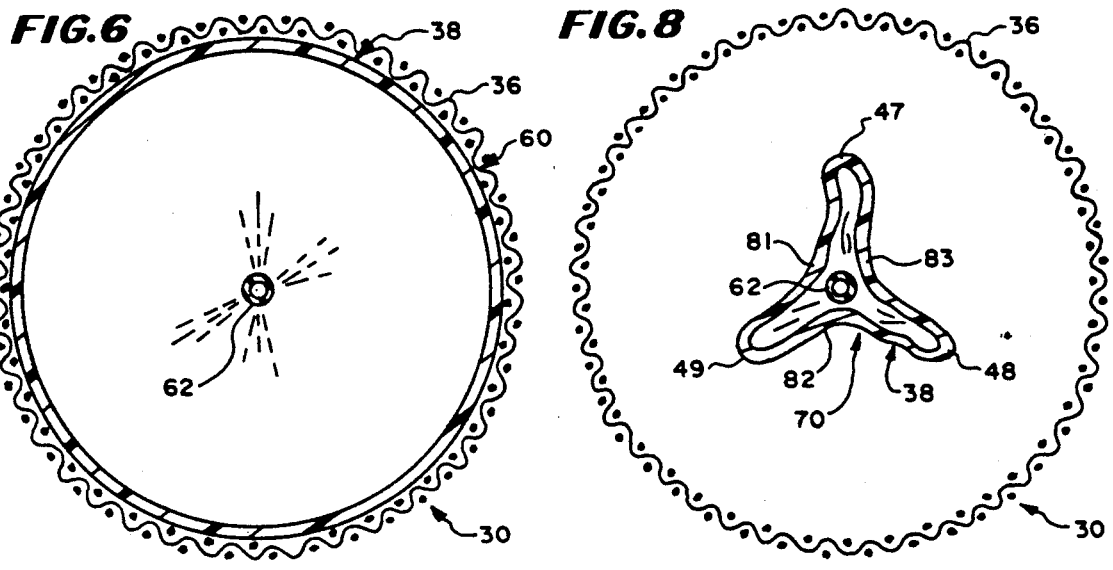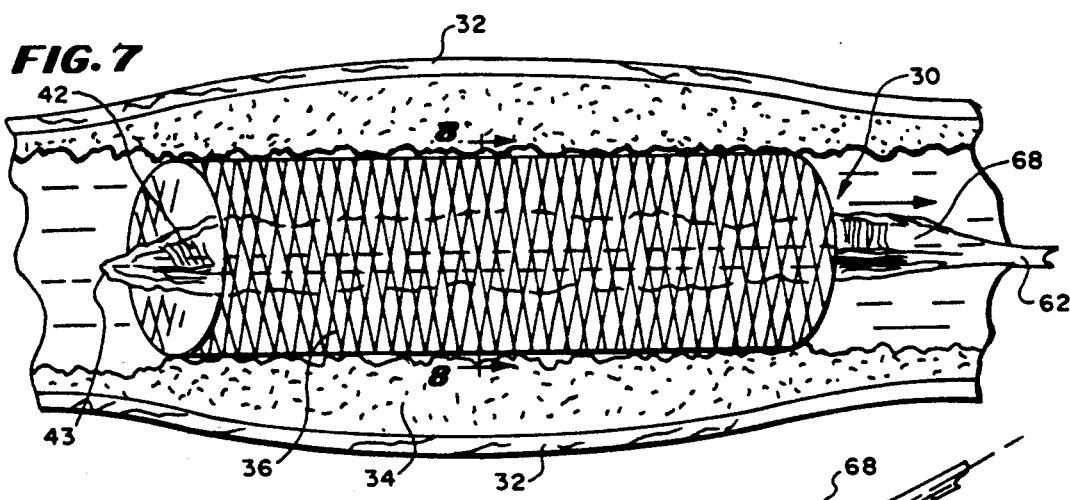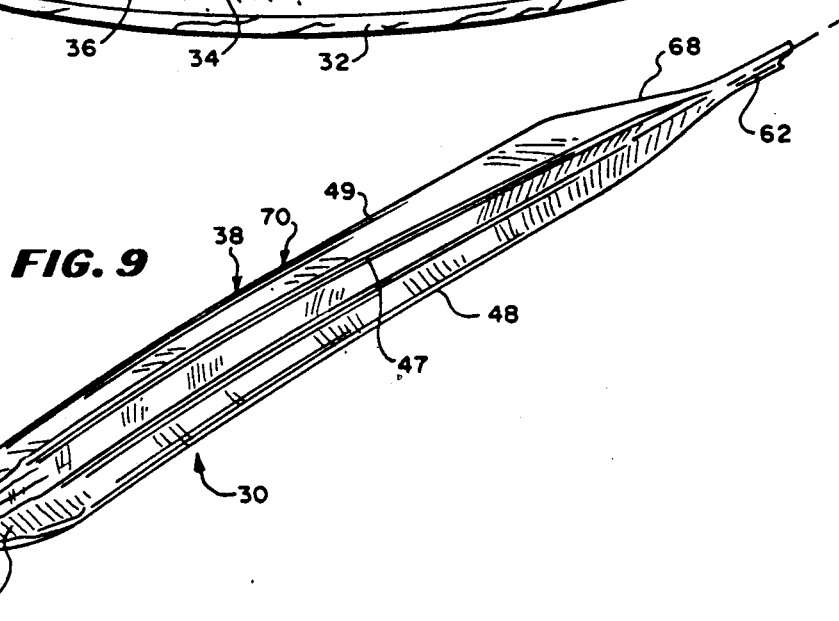

STENT-IMPLANTING BALLOON ASSEMBLY

BACKGROUND OF THE INVENTION

1. Field of the Invention

The present invention relates to a dilatation balloon assembly utilized for the implantation of an endoprosthesis device, such as a stent, within a vessel such as a blood vessel in a living body.

2. Description of the Prior Art

Recently endoprosthesis devices, such as stents, have come into more common use in treating stenosis strictures or aneurysms in a blood vessel. Such a device or stent is implanted within a vascular system to reinforce a collapsing, partially occluded or abnormally dilatated section of the blood vessel or to effect and reestablish a connection between blocked vessels.

A common procedure for implanting a stent is to first open the region of the vessel with a dilatation balloon catheter. Then, a stent is positioned in the opened area in a position to bridge the opened area, which may be a weakened portion of a blood vessel or an opened area of reconnection between blood vessels.

In the field of angioplasty where a dilatation balloon catheter is placed in a constricted stenotic region and then inflated to expand and open that region, it has been found that the dilatating or opening of the restricted stenotic region, while initially relieving the problem of an occluded restricted passageway in the vessel, does not provide a sufficiently long term solution to the problem. In this respect, after a relatively short period of time of a few years the vessel often returns to its original occluded state, i.e., postangioplasty restenosis, as a result of the blood vessel collapsing inwardly or as a result of the rebuilding of plaque in the stenotic region.

What has proved to be more successful is the implantation of a stent after the restricted stenotic region has been dilatated. Recent studies indicate that by use of a stent the constriction of the blood vessel in the region of stenotic restriction is maintained open for a much longer period of time than with dilatation alone. Articles describing the procedures used and the results obtained are set forth below:

"Expandable Intrahepatic Portacaval Shunt Stents", Palmaz et al "AJR: 145", pp. 821–825. October 1985

"Expandable Intraluminal Graft: A Preliminary Study", Palmaz et al, Vol. 156, No. 1, pp. 73–77, "Radiology", July 1985

"The Palmaz Stent: A Possible Technique for Prevention of Postangioplasty Restenosis", Levin, Volume 169, pp. 87374, "Radiology" September 1988

"Intraluminal Stents in Atherosclerotic Iliac Artery Stenosis: Preliminary Report of a Multicenter Study", Palmaz et al, Volume 168, pp. 727–731, "Radiology", September 1988

As a result, there is an increasing use of stents and dilatation balloon assemblies for implanting stents.

Examples of prior art stents can be found in the following U.S. patents:

| U.S. Pat. No. | Patentee |
| --- | --- |
| 4,140,126 | Chaudhury |
| 4,503,569 | Dotter |
| 4,733,665 | Palmaz |
| 4,776,337 | Palmaz |
| 4,795,458 | Regan |
| 4,880,882 | Gianturco |

Examples of typical prior art dilatation balloon catheter assemblies can be found in the Gruntzig et al. U.S. Pat. No. 4,195,637 and the Simpson et al. U.S. Pat. No. 4,323,071, the disclosures of which are incorporated herein by reference.

A common problem that has been incurred with the use of dilatation balloon assemblies for implantation of and placement of a stent is the inability of the deflated balloon to disengage from the stent after the stent has been expanded. This phenomena is found most frequently in P.E.T. balloons where the balloon, upon collapsing, tends to flatten out under negative pressure producing a flat or "wing-like" configuration which is wider than the inflated diameter of the balloon ($\pi R$).

In this respect, a 3.0 mm balloon can produce a 4.7 mm wide plane when it is collapsed.

In addition to the disengagement problem found during the stent implanting or placement, the edges of the wings are "blade-like" and sharp enough to cause serious damage to severely diseased (and even healthy) vessels when the deflated, flattened "wing-like" balloon is withdrawn from a blood vessel in a PTCA procedure.

As will be described in greater detail hereinafter, the present invention provides a balloon design for a dilatation balloon assembly which results in the balloon having a lateral or cross-sectional extent when it is partially collapsed or fully collapsed, which is less than the diameter of the fully inflated balloon which assumes a generally cylindrical shape. In this way, the creation of a "wing-like" or "blade-like" deflated balloon with sharp edges and with a width or lateral extent greater than the inner diameter of the stent or of the blood vessel through which it is drawn is eliminated, thereby minimizing if not altogether eliminating the possibility of trauma to the blood vessel when the collapsed/deflated balloon is withdrawn from the stent and the vessel.

SUMMARY OF THE INVENTION

According to the present invention there is provided a dilatation balloon assembly comprising a catheter having a generally cylindrical side wall, a proximal end, a distal end and a distal end portion. The distal end portion has openings in the side wall thereof, and a dilatation balloon is connected to and extends from the distal end of the catheter around and about the distal end portion of the catheter to a proximal end of the balloon which is also connected to the catheter. The balloon has at least three longitudinal creases therein whereby the balloon, in a partially inflated state or deflated state, is noncircular in cross-section and, in an inflated state, is generally circular in cross-section, and whereby when the dilatation balloon is in a partially inflated state or deflated state, the lateral extent of the dilatation balloon is less than the diameter or lateral extent of the fully inflated balloon.

Further according to the invention there is provided a stent-implanting balloon assembly comprising a dilatation balloon assembly including a catheter having a generally cylindrical side wall, a proximal end, a distal end and a distal end portion. The distal end portion has openings in the side wall thereof. A dilatation balloon is connected to and extends from the distal end of the catheter around and about the distal end portion of the catheter to a proximal end of the balloon which is also connected to the catheter. A cylindrical expandable/collapsible stent is received and mounted on the balloon. The balloon has at least three longitudinal creases therein whereby the balloon in a partially inflated state or deflated state and positioned within the stent is noncircular in cross-section, and in an inflated state, is generally circular in cross-section, and whereby when said balloon is in a deflated state the maximum lateral extent in cross-section of the balloon is less than the diameter or lateral extent of a fully inflated balloon or partially inflated balloon and less than the diameter of the expanded stent.

BRIEF DESCRIPTION OF THE DRAWINGS

FIG. 1A is a fragmentary perspective view, with portions broken away, of an expanded prior art balloon, within a prior art stent within a blood vessel.

FIG. 1B is a fragmentary perspective view, with portions broken away, of the blood vessel shown in FIG. 1 with the prior art stent therein and with the prior art balloon partially collapsed.

FIG. 1C is a fragmentary perspective view of the prior art stent and balloon assembly shown in FIG. 1 within the blood vessel shown in FIG. 1 with portions broken away and shows the balloon collapsed within the stent and shows the folded flat portions of the balloon slightly curved as a result of the inner diameter of the stent being less than the lateral extent of the collapsed balloon.

FIG. 2 is an axial longitudinal sectional view through a blood vessel in a living body and shows an axial longitudinal sectional view of a stent mounted on a stent-implanting balloon assembly constructed according to the teachings of the present invention and inserted in the vessel in an area of stenosis.

FIG. 3 is a sectional view of the stent placement balloon assembly of the present invention with a stent therearound and is taken along lines 3—3 of FIG. 2.

FIG. 4 is a sectional view through a portion of a partially expanded stent mounted on a partially expanded stent placement balloon assembly of the present invention.

FIG. 5 is an axial longitudinal sectional view of an expanded stent and an expanded stent-implanting balloon assembly in the blood vessel shown in FIG. 2.

FIG. 6 is a perspective view of the stent and balloon assembly with the balloon of the assembly substantially completely collapsed.

FIG. 7 is a transverse sectional view of the expanded stent and expanded stent-implanting balloon assembly shown in FIG. 5 and is taken along line 6—6 of FIG. 5.

FIG. 8 is a transverse sectional view of the expanded stent and deflated stent-implanting balloon assembly, similar to the view shown in FIG. 6, and is taken along line 8—8 of FIG. 7.

FIG. 9 is a perspective view of one preferred embodiment of the stent-implanting balloon assembly of the present invention, this embodiment also being shown in FIG. 4, and shows the balloon of the assembly with a slight twist or spiral at the longitudinal edges of the triangular-in-cross-section balloon which facilitates a spiral or "unthreading" movement of the balloon assembly out of a vessel.

DESCRIPTION OF THE PREFERRED EMBODIMENT

Referring now to the drawings in greater detail, there is illustrated in FIGS. 1A–1C a perspective view of a prior art stent-implanting balloon assembly 10 in a vessel 12 with a stent 14 around a balloon 16 of the assembly 10. A portion of the blood vessel 12 is cut away to show the inflated balloon 16 of the balloon assembly 10 within the stent 14.

FIG. 1A shows the stent 14 in the expanded position thereof as a result of the inflation of the balloon 16 of the balloon assembly 12.

The balloon assembly 10 includes not only the balloon 16 but also an inflation tube, lumen, or catheter 17 disposed within the balloon 16 and having ports (not shown) in the side thereof. The balloon 16 is generally cylindrical in shape (circular in cross-section) and, when fully inflated, as shown in FIG. 1A, assumes a cylindrical shape forcing the stent 14 cylindrically outwardly against the inner wall of the vessel 12.

As shown in FIG. 1B, when the balloon 16 is deflated and collapses, it tends to assume a flat, elongate shape 18 with the width of the flat collapsed balloon 18 being greater than the inner diameter of the stent 14 and often times greater than the diameter of the vessel 12 through which the collapsed balloon 18 must now be withdrawn.

Side edges 20 and 22 of the collapsed balloon 18 tend to bear against the inner wall 24 of the stent 14 as shown in FIG. 1B tending to prevent withdrawal of the deflated balloon 18. The deflated balloon 18 also will tend to bear against the wall of a vessel, e.g. vessel 12, through which the collapsed balloon 18 is withdrawn.

As shown in FIG. 1C, the collapsed balloon 18 by having a greater width than the diameter of the stent 14 will tend to assume a curved shape. However, the elasticity of the collapsed balloon 18 will continue to exert some outward pressure at the edges 20, 22 of the collapsed balloon 18 against the stent 14 and against the vessel 12 through which it is withdrawn.

Although the balloon 16 is made of an elastic material, the edges of the collapsed balloon 18 have a certain degree of sharpness or "blade-like structure" which can result in abrasion to or cutting of the walls of the vessel 12, such as a blood vessel, when the collapsed balloon 18 is withdrawn from a living body. Accordingly, prior art stent-implanting balloon assemblies have been susceptible of causing injury to blood vessels. This susceptibility to causing injury to blood vessels is minimized, if not altogether eliminated, in the stent-implanting balloon assembly 30 of the present invention shown in FIGS. 2-9.

Referring to FIG. 2 in greater detail, there is illustrated therein an axial longitudinal sectional view through a blood vessel 32 having an area of stenosis 34 and shows a perspective view of a stent 36 mounted on a balloon 38 of the balloon assembly 30 of the present invention positioned within the area of stenosis 34.

As shown, the partially-inflated balloon assembly 30 has a generally pointed, pyramid shaped tip portion 42 which has a pointed tip 43 and which has a transverse generally triangular cross-section, (FIG. 4) formed by creases in the tip portion 42 which extend to axially extending, longitudinal creases or edges 47, 48 and 49 (FIG. 4) placed in the balloon 38 of the assembly 30 in accordance with the teachings of the present invention.

Likewise, the remainder of the balloon 38 along the length thereof is generally triangular in cross-section as shown in FIGS. 3 and 4. This results in a length between a corner crease or edge 47, 48 or 49 and one side 51, 52 or 53 (FIG. 4) of a partially inflated balloon 50 which is not greater than the inner diameter of a partially expanded stent 55 or of the cylindrical shape of an inflated balloon 60 (when fully inflated) as shown in FIGS. 5 and 6.

The distance between the edges 47, 48 and 49 is even less when the balloon 38 is collapsed or deflated to a triangular shape 70 as shown in FIGS. 3 and 8.

As shown in phantom in FIG. 2 the balloon assembly 30 includes a central tube, conduit or catheter 62 therein having a plurality of side ports 64 to facilitate inflation and expansion of the balloon 38, as well as evacuation, deflation and collapsing of the balloon 38. The distal tip portion 42 of the balloon 38 tapers in a pyramid shape to and is integral with a distal end 66 of the catheter 62 as shown in phantom in FIGS. 2, 5 and 7. Also, a proximal portion 68 of the balloon 50 tapers to and is integral with the catheter 62 which extends out through the vessel 32 and out of the living body 38 as shown in FIGS. 3, 5, 7, and 9.

In one balloon assembly 30, and with reference to FIGS. 4, 6 and 8 respectively, the distance H between the corner crease 47 and side 51 in a partially inflated balloon 50 (FIG. 4) is 2.7 mm, the distance D, the diameter of an inflated balloon 60 (FIG. 6), is 3.0 mm and the distance X, the maximum lateral extent of a collapsed balloon 70 (FIG. 8), is 2.0 mm. The stent 36 is generally cylindrical and comprises an expandable/collapsible cross wire mesh of criss-crossing wire coils that make a small angle to an axial plane passing through the stent 36 when the stent 36 is stretched axially to its smallest diameter and which criss-crossing wire coils make a large angle to an axially extending plane through the stent 36 when the stent 36 is axially compressed to expand the coils radially outwardly to a large diameter of the stent 36.

In the use of the stent-implanting balloon assembly 30, the balloon 38 of the assembly 30 is inserted in the stent 36 as shown in FIG. 2 to hold the stent 36 on the balloon 50. Then, the stent 36 and balloon assembly 30 are inserted through the vessel 32, to a desired position in the area of stenosis 34 as shown in FIG. 2.

The balloon 38 is then fully inflated to the cylindrical shape 60 shown in FIG. 6 for expanding the stent 36 to the desired cylindrical shape 60 shown in FIG. 6.

Next, the balloon 38 is evacuated or deflated and collapsed so that the partially collapsed balloon 50 (FIG. 4) or the fully collapsed balloon 70 (FIGS. 7 and 8) can be withdrawn from the stent 36 and through the vessel 32. In the evacuated collapsed state, as shown in FIGS. 7 and 8, the balloon 70 will assume a generally Y shape where the distance between adjacent ends of the Y and the distance X between one end of the Y and a plane passing through the other two ends of the Y will be less than the diameter of the stent 36 (expanded or unexpanded) and less than the diameter of the vessel 32 through which the collapsed balloon 70 is retracted. As a result, the corner creases or edges 47, 48 49 will not be pressed against the inner side wall of the vessel 32 by the elasticity of the collapsed portions 81, 82, 83 of the balloon 70, which results in the minimizing of trauma or damage to the blood vessel 32 through which the balloon 70 is retracted.

In FIGS. 4 and 9, there is illustrated one preferred balloon assembly 30 wherein the balloon 38 in its deflated state (FIG. 9) or in its partially inflated state (FIG. 4) has a generally triangular cross-section defined by the axially extending, longitudinal edges or creases 47, 48, 49 of the balloon 38 which extend in a slight spiral about the elongate axis of the balloon 38 so that the collapsed balloon 38 can be "unthreaded" out of the vessel by twisting of, as well as by pulling on, the proximal end of the catheter 62 of the balloon assembly 30.

If desired, a larger angle of spiral can be provided to provide a greater threading or unthreading action upon axial movement of or rotation of the catheter 60 in one direction or the other direction.

From the foregoing description, it will be apparent that the stent-implanting balloon assembly 30 of the present invention has a number of advantages, some of which have been described above and others which are inherent in the invention.

For example, the generally triangular cross-section of the partially inflated balloon 50 and subsequently the collapsed Y-shaped balloon 70 provides a programmed, uniform collapse when negative pressure is applied, improving disengagement from the stent 36.

The reduced profile of the deflated balloon 70 provides a less traumatic surface, thus reducing potential damage to a diseased or a healthy vessel through which the deflated/collapsed balloon 70 is withdrawn. Such reduced profile also facilitates withdrawal into a guiding catheter.

The collapsed Y-shaped triangular balloon configuration 70 and partially inflated triangular balloon configuration 50 provides more uniform corner edges for mounting the stent 36.

Finally, the triangular cross-section balloon 50 can be used in other applications, such as valvuloplasty, in addition to stent-implanting and placement.

Also, it will be understood that modifications can be made to the stent-implanting balloon assembly 30 of the present invention without departing from the teachings of the present invention. Accordingly, the scope of the invention is only to be limited as necessitated by the accompanying claims.

I claim:

1. A dilatation balloon assembly comprising a catheter having a generally cylindrical side wall, a proximal end, a distal end and a distal end portion, the distal end portion having openings in the side wall thereof, and a single lumen dilatation balloon connected to and extending from the distal end of said catheter around and about said distal end portion of the catheter to a proximal end of said balloon which is also connected to said catheter, said dilatation balloon having at least three longitudinal creases in the outer wall thereof whereby said balloon, in a partially inflated state or deflated state, is noncircular in cross-section and, in an inflated state, is generally circular in cross-section, and whereby, when said balloon is in a deflated state with a noncircular, generally triangular or "Y" shape, the maximum lateral extent in cross-section of the dilatation balloon is less than the diameter or lateral extent of a fully inflated balloon or a partially inflated balloon.

2. The dilation balloon assembly of claim 1 wherein said longitudinal creases set in said balloon are equidistant from each other such that, when said balloon is partially inflated, said balloon assumes a generally triangular cross-section and when deflated said balloon has a generally Y shape cross-section.

3. The dilatation balloon assembly of claim 1 wherein said longitudinal creases are skewed so as to extend in a spiral path about said catheter whereby said deflated balloon can be withdrawn from a vessel in a "threaded" manner.

4. A stent-implanting balloon assembly comprising a dilatation balloon assembly including a catheter having a generally cylindrical side wall, a proximal end, a distal end and a distal end portion, said distal end portion having openings in the side wall thereof, a single lumen dilatation balloon connected to an extending from the distal end of said catheter around and about said distal end portion of said catheter to a proximal end of said balloon which is also connected to said catheter, and a cylindrical expandable/collapsible stent received and mounted on said balloon, said balloon having at least three longitudinal creases in the outer wall thereof whereby said balloon, in a partially inflated state or deflated state and positioned within said stent, is noncircular in cross-section and, in an inflated state is generally circular in cross-section, and whereby, when the balloon is in a deflated state with a noncircular, generally triangular or "Y" shape, the maximum lateral extent in cross-section of the balloon is less than the diameter or lateral extent of a fully inflated balloon or a partially inflated balloon and less than the diameter of the expanded stent.

5. The stent-implanting balloon assembly of claim 4 wherein said longitudinal creases set in said balloon are equidistant from each other such that, once said balloon is partially inflated, said balloon assumes a generally triangular cross-section and when deflated said balloon has a generally "Y" shape cross-section.

6. The stent-implanting balloon assembly of claim 4 wherein said longitudinal creases are skewed so as to extend in a spiral path about said catheter whereby said deflated balloon can be advanced or withdrawn from a vessel in a "threaded" manner.

7. The stent-implanting balloon assembly of claim 4 wherein said balloon is constructed with only one balloon compartment for receiving dilatation fluid.

8. The stent-implanting balloon assembly of claim 4 wherein said cylindrical expandable/collapsible stent is a cross wire mesh of criss-crossing wire coils that make a small angle to an axial plane passing through the stent when the stent is stretched axially to its smallest diameter and which criss-crossing wire coils make a large angle to an axially extending plane through the stent when the stent is axially compressed to expand the coils radially outwardly to a large diameter of the stent.

9. The dilatation balloon assembly of claim 1 wherein said balloon is constructed with only one balloon compartment for receiving dilatation fluid.

* * * * *